United States Patent [19]

Torii et al.

[11] Patent Number: 5,204,458
[45] Date of Patent: Apr. 20, 1993

[54] PROCESS FOR PREPARING CEPHEM DERIVATIVES

[75] Inventors: Sigeru Torii, Akaiwa; Hideo Tanaka, Oakayama; Masatoshi Taniguchi, Osaka; Michio Sasaoka, Tokushima; Takashi Shiroi, Tokushima; Yutaka Kameyama, Tokushima, all of Japan

[73] Assignee: Otsuka Kagaku Kabushiki Kaisha, Osaka, Japan

[21] Appl. No.: 849,160

[22] Filed: Mar. 10, 1992

[30] Foreign Application Priority Data

Mar. 11, 1991 [JP] Japan .................................. 3-72450

[51] Int. Cl.$^5$ .......................................... C07D 501/02
[52] U.S. Cl. ................... 540/222; 540/215; 540/221; 540/225; 540/227
[58] Field of Search ............... 540/215, 227, 222, 225, 540/221

[56] References Cited

U.S. PATENT DOCUMENTS 4,656,264 4/1987 Torii et al. ...................... 540/215

Primary Examiner—Nicholas S. Rizzo
Attorney, Agent, or Firm—Armstrong, Westerman, Hattori, McLeland & Naughton

[57] ABSTRACT

The present invention provides a process for preparing a cephem derivative characterized in that an allenyl β-lactam compound represented by the formula (1)

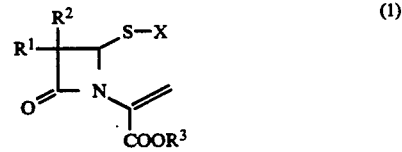

(1)

wherein $R^1$ is amino or protected amino, $R^2$ is a hydrogen atom or lower alkoxyl, $R^3$ is a hydrogen atom or carboxylic acid protecting group and X is the group $-SO_2R^4$ or $-SR^4$, $R^4$ being substituted or unsubstituted aryl or substituted or unsubstituted nitrogen-containing aromatic heterocyclic group is reacted with a nucleophilic agent to obtain the derivative, the cephem derivative being represented by the formula (2)

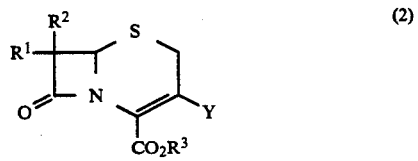

(2)

wherein $R^1$, $R^2$ and $R^3$ are as defined above, and Y is the residue of the nucleophilic agent.

1 Claim, No Drawings

PROCESS FOR PREPARING CEPHEM DERIVATIVES

The present invention relates to a novel process for preparing cephem derivatives.

J. Org. Chem., 54, 4962 (1989) discloses a process which is heretofore known and which has found wide use for preparing cephem derivatives represented by the formula (2)

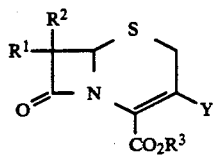
(2)

wherein $R^1$ is amino or protected amino, $R^2$ is a hydrogen atom or lower alkoxyl, $R^3$ is a hydrogen atom or carboxylic acid protecting group and Y is the residue of a nucleophilic agent.

Generally when a nucleophilic agent is reacted with a compound of the formula (2) wherein Y is a halogen atom or mesyloxy, a Δ2-cephem compound of the formula (3)

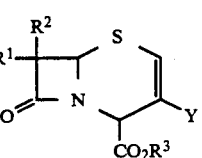
(3)

wherein $R^1$, $R^2$, $R^3$ and Y are as defined above is formed as a by-product. To avoid this problem, the disclosed process uses a 3-hydroxycephem compound of the formula (2) wherein Y is hydroxyl, with which a nucleophilic agent is reacted after the hydroxyl of the compound has been converted to trifluoromesyloxy as described in the literature. However, the 3-hydroxycephem compound used as the starting material is difficult to synthesize, while expensive trifluoromethanesulfonic anhydride is also used in the process. Because of these drawbacks, the process is in no way satisfactory as a practically useful process.

An object of the present invention is to provide a universal process for preparing the above-mentioned cephem derivative in a high yield with high purity free of the drawbacks of the conventional process.

The above and other objects of the invention will become apparent from the following description.

The present invention provides a process for preparing a cephem derivative characterized in that an allenyl β-lactam compound represented by the formula (1)

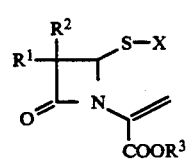
(1)

wherein R is amino or protected amino, $R^2$ is a hydrogen atom or lower alkoxyl. $R^3$ is a hydrogen atom or carboxylic acid protecting group and X is the group —$SO_2R^4$ or —$SR^4$, $R^4$ being substituted or unsubstituted aryl or substituted or unsubstituted nitrogen-containing aromatic heterocyclic group is reacted with a nucleophilic agent to obtain the derivative, the cephem derivative being represented by the formula (2).

The allenyl β-lactam compound represented by the formula (1) and useful as the starting material of the invention is a novel compound which has not been disclosed in literature and can be prepared, for example, by reacting a base with an azetidinone derivative represented by the formula (4)

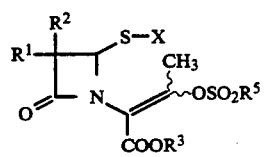
(4)

wherein $R^1$, $R^2$, $R^3$ and X are as defined above, and $R^5$ is substituted or unsubstituted lower alkyl or substituted or unsubstituted aryl.

The azetidinone derivative represented by the formula (4) is prepared, for example, by the process disclosed in JP-A-165367/1986.

Examples of groups mentioned herein are as follows. The term "halogen atom" as used hereinafter means, for example, fluorine, chlorine, bromine or iodine atom unless otherwise specified. The term "lower alkyl" means a straightchain or branched $C_{1-4}$ alkyl group such as methyl, ethyl, n-propyl, isopropyl, n-butyl, isobutyl, sec-butyl or tert-butyl. The term "aryl" means, for example, phenyl, naphthyl or the like.

Exemplary of the protected amino represented by $R^1$ are phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, phenylacetoxyacetamido, α-oxophenylacetamido, thienylacetamido, benzamido, p-methylbenzamido, p-tert-butylbenzamido, p-methoxybenzamido, p-chlorobenzamido and p-bromobenzamido groups, the groups disclosed in Theodora W. Greene, "Protective Groups in Organic Synthesis" (hereinafter referred to merely as the "literature"), Chap. 7 (pp. 218-287), phenylglycylamido group, phenylglycylamido groups having protected amino, p-hydroxyphenylglycylamido group, and p-hydroxyphenylglycylamido groups having protected amino and/or protected hydroxyl. Examples of protective groups for amino are those disclosed in the literature, Chap. 7 (pp. 218-287). Examples of protective groups for the hydroxyl of p-hydroxyphenylglycylamido group are those disclosed in the literature, Chap. 2 (pp. 10-72).

Exemplary of the lower alkoxyl represented by $R^2$ are straight-chain or branched $C_{1-4}$ alkoxyl groups such as methoxy, ethoxy, n-propoxy isopropoxy, n-butoxy, isobutoxy sec-butoxy and tert-butoxy groups.

Exemplary of the carboxylic acid protecting group represented by $R^3$ are benzyl, p-methoxybenzyl, p-nitrobenzyl, diphenylmethyl, trichloroethyl, tert-butyl, and those disclosed in the literature, Chap. 5 (pp. 152-192).

While $R^4$ represents a nitrogen-containing aromatic heterocyclic group which may have a substituent or substituents, exemplary of the nitrogen-containing aromatic hetrocyclic group are thiazol-2-yl, thiadiazol-2-yl, benzothiazol-2-yl, oxazol-2-yl, benzoxazol-2-yl, imidazol-2-yl, benzoimidazol-2-yl, pyrimidinyl, pyridyl and the like.

Exemplary of the substituent which may be substituted in the aryl or nitrogen-containing aromatic heterocyclic group represented by $R^4$ are halogen atoms, hydroxyl, nitro, cyano, aryl, lower alkyl, amino, mono lower alkylamino, di lower alkylamino, mercapto, alkylthio or arylthio represented by the group $R^6S—$ (wherein $R^6$ is lower alkyl or aryl), formyloxy, acyloxy represented by the group $R^6COO—$ (wherein $R^6$ is as defined above), formyl, acyl represented by the group $R^6CO—$ (wherein $R^6$ is as defined above), alkoxyl or aryloxy represented by $R^6O—$ (wherein $R^6$ is as defined above), carboxyl, alkoxycarbonyl or aryloxycarbonyl represented by the group $R^6OCO—$ (wherein $R^6$ is as defined above), etc. The aryl or nitrogen-containing aromatic heterocyclic group represented by $R^4$ may have one or at least two same or different groups selected from among the above substituents.

$R^5$ represents lower alkyl or aryl which may have a substituent or substituents, examples of which are those mentioned for $R^4$. The lower alkyl or aryl represented by $R^5$ may have one or at least two same or different groups selected from among the foregoing substituents. Such substituent(s) may be positioned on at least one carbon atom of the alkyl or aryl.

Examples of residues of nucleophilic agents represented by Y are halogen atoms, hydroxyl, azido, cyano, isocyano, the group $—OR^7$ (wherein $R^7$ is substituted or unsubstituted lower alkyl or substituted or unsubstituted aryl), the group $—OCOR^7$ (wherein $R^7$ is as defined above), the group $—SCSOR^7$ (wherein $R^7$ is as defined above), the group $—SCSN(R^7)_2$ (wherein $R^7$ is as defined above), the group $—NHR^7$ (wherein $R^7$ is as defined above), the group $—N(R^7)_2$ (wherein $R^7$ is as defined above), the group $—SO_2R^7$ (wherein $R^7$ is as defined above), the group $—SR^8$ (wherein $R^8$ is substituted or unsubstituted lower alkyl, substituted or unsubstituted aryl, or substituted or unsubstituted nitrogen-containing aromatic heterocyclic group), nitrogen-containing heterocyclic group having a free electron-pair on nitrogen which may have a substituent.

Examples of nitrogen-containing heterocyclic groups which have a free electron-pair on nitrogen and which may have a substituent are piperidino, morpholino, 1-piperazinyl, 1-pyrrolidinyl, 1-imidazolidinyl, 1-pyrazolidinyl, 2-pyrrolin-1-yl, 2-imidazolin-1-yl, 3-pyrazolin-1-yl, 1-indolinyl, 2-indolinyl, 1-pyrrolyl, 1-indolyl, 2-isoindolyl, 1-imidazolyl, 1-pyrazolyl, 1-benzimidazolyl, 1H-1-indazolyl, 1-triazolyl, 1-tetrazolyl, phthaloyl and the like.

Exemplary of the substituted or unsubstituted nitrogen-containing aromatic heterocyclic group represented by $R^8$ are those exemplified for the nitrogen-containing aromatic heterocyclic group represented by $R^4$.

Examples of substituents for the nitrogen-containing heterocyclic group represented by Y, the lower alkyl or aryl represented by $R^7$ and the lower alkyl, aryl or nitrogen-containing aromatic heterocyclic group represented by $R^8$ are the same substituents as those exemplified for $R^4$. The nitrogen-containing heterocyclic group represented by Y, the lower alkyl or aryl represented by $R^7$ and the lower alkyl, aryl or nitrogen-containing aromatic heterocyclic group represented by $R^8$ may have same or different substituents selected from among these examples, as positioned on at least one atom of the group.

To prepare the allenyl β-lactam compound of the formula (1) to be used as a starting material according to the invention, the azetidinone derivative of the formula (4) is reacted with a base in a suitable solvent. The base to be used is preferably an aliphatic or aromatic amine. Examples of such amines are triethylamine, diisopropylamine, ethyldiisopropylamine, tributylamine, DBN(1,5-diazabicyclo[3.4.0]nonene-5), DBU(1,8-diazabicyclo[5.4.0]undecene-7), DABCO(1,4-diazabicyclo[2.2.2]octane), piperidine, N-methylpiperidine, 2,2,6,6-tetramethylpiperidine, morpholine, N-methylmorpholine, N,N-dimethylaniline, N,N-dimethylaminopyridine and the like.

The base is used usually in an amount of 1 to 12 moles, preferably 1 to 6 moles, per mole of the compound of the formula (4). The solvent to be used can be any of a wide variety of those which dissolve the compound of the formula (4) and which are inert under the reaction condition employed. Examples of useful solvents are lower alkyl esters of lower carboxylic acids such as methyl formate, ethyl formate, propyl formate, butyl formate, methyl acetate, ethyl acetate, propyl acetate, butyl acetate, methyl propionate and ethyl propionate; ethers such as diethyl ether, ethyl propyl ether, ethyl butyl ether, dipropyl ether, diisopropyl ether, dibutyl ether, methyl cellosolve and dimethoxyethane; cyclic ethers such as tetrahydrofuran and dioxane; nitriles such as acetonitrile, propionitrile, butyronitrile, isobutyronitrile and valeronitrile; substituted or unsubstituted aromatic hydrocarbons such as benzene, toluene, xylene, chlorobenzene and anisole; hydrocarbon halides such as dichloromethane, chloroform, dichloroethane, trichloroethane, dibromoethane, propylene dichloride, carbon tetrachloride and chloroiluoroalkane; hydrocarbons such as pentane, hexane, heptane and octane; cycloalkanes such as cyclopentane, cyclohexane, cycloheptane and cyclooctane; amides such as dimethylformamide and dimethylacetamide; dimethyl sulfoxide; etc. These solvents are used singly or in admixture. The solvent may contain water. The solvent is used preferably in an amount of about 0.5 to about 200 liters, more preferably about 1 to about 50 liters, per kg of the compound of the formula (4). The reaction is conducted at $-70°$ C. to $100°$ C., preferably $-50°$ C. to $50°$ C.

According to the present invention, the allenyl β-lactam compound represented by the formula (1) and prepared from the compound of the formula (4) by the foregoing process is isolated by extraction or like usual method and thereafter reacted as it is with a nucleophilic agent without resorting to any special purification method, whereby the lactam compound can be converted to the cephem derivative represented by the formula (2).

The nucleophilic agent for use in the present invention is represented by the formula Y—H (wherein Y is as defined above). According to the invention, the compound of the formula (1) is reacted with the nucleophilic agent Y—H directly or in the presence of a base. Use of an additive, such as a halide, oxide, sulfate or nitrate of an alkaline earth metal, is likely to achieve an improved yield.

The nucleophilic agent represented by Y—H is used usually in an amount of 1 to 50 moles, preferably about 1 to about 10 moles, per mole of the compound of the formula (1). If Y in the agent is the same as X in the starting material, the amount may be up to 1 mole.

Examples of bases for use in the above reaction are lithium hydroxide, sodium hydroxide, potassium hydroxide and like hydroxides of alkali metals, lithium carbonate, sodium carbonate, potassium carbonate and like alkali metal carbonates, lithium bicarbonate, sodium bicarbonate, potassium bicarbonate and like alkali metal bicarbonates, lithium oxides, sodium oxide, potassium oxide and like alkali metal oxides, lithium hydride, sodium hydride, potassium hydride and like alkali metal hydride, methyllithium, butyllithium and like lower alkyl lithium salts, phenyllithium and like aryl lithium salts, magnesium hydroxide, calcium hydroxide, strontium hydroxide, barium hydroxide and like alkaline earth metal hydroxides, magnesium carbonate, potassium carbonate, strontium carbonate, barium carbonate and like alkaline earth metal carbonates, magnesium oxide, calcium oxide, strontium oxide, barium oxide and like alkaline earth metal oxides, magnesium hydride, calcium hydride and like alkaline earth metal hydride, ammonium, methylamine, ethylamine, ispropylamine, diethylamine, diisopropylamine, triethylamine, tributylamine, ethyldiisopropylamine, piperidine, N-methylpiperidine, morpholine, N-methylmorpholine, N,N-dimethylaniline, aniline, pyridine, N,N-dimethylaminopyridine, DBN(1,5-diazabicyclo[3.4.0]nonene-5), DBU(1,8-diazabicyclo[5.4.0]undecene-7), DABCO(1,4-diazabicyclo[2.2.2]octane) and like amines, etc. The base to be used is suitably selected depending on the kind of nucleophilic agent Y—H used.

The base is used in an amount usually of 0.01 to 50 moles, preferably about 0.1 to about 10 moles, per mole of the compound of the formula (1). The nucleophilic agent Y—H can be reacted with the base before the reaction, or a salt of Y—H and base is alternatively usable. The salt of nucleophilic agent and base, when to be used, is used usually in an amount of 1 to 50 moles, preferably about 1 to about 10 moles, per mole of the compound of the formula (1).

Examples of alkaline earth metal halides, oxides, sulfates and nitrates which may be added to the reaction system are magnesium halides, calcium halides, strontium halides, barium halides and like halides, magnesium oxide, calcium oxide, strontium oxide, barium oxide and like oxides, magnesium sulfate, calcium sulfate, strontium sulfate, barium sulfate and like sulfates, and magnesium nitrate, calcium nitrate, strontium nitrate, barium nitrate and like nitrates. The additive to be used is suitably selected depending on the kind of nucleophilic agent Y—H used.

The additive is used generally in an amount of 0.01 to 100 moles, preferably about 0.1 to about 50 moles, per mole of the compound of the formula (1).

The above reaction is conducted usually in a solvent. The solvent to be used can be any of a wide variety of those known in the art which dissolve the compound of the formula (1) and which are inert under the reaction condition employed. Examples of useful solvents are alcohols such as methanol, ethanol, propanol, isopropanol, butanol and tert-butanol; lower alkyl esters of lower carboxylic acids such as methyl formate, ethyl formate, propyl formate, butyl formate, methyl acetate, ethyl acetate, propyl acetate, butyl acetate, methyl propionate and ethyl propionate; ketones such as acetone, methyl ethyl ketone, methyl isopropyl ketone, methyl butyl ketone, methyl isobutyl ketone and diethyl ketone; ethers such as diethyl ether, ethyl propyl ether, ethyl butyl ether, dipropyl ether, diisopropyl ether, dibutyl ether, methyl cellosolve and dimethoxyethane; cyclic ethers such as tetrahydrofuran and dioxane; nitriles such as acetonitrile, propionitrile, butyronitrile, isobutyronitrile and valeronitrile; substituted or unsubstituted aromatic hydrocarbons such as benzene, toluene xylene, chlorobenzene and anisole; hydrocarbon halides such as dichloromethane, chloroform, dichloroethane, trichloroethane, dibromoethane, propylene dichloride, carbon tetrachloride and Freons; hydrocarbons such as pentane, hexane, heptane and octane; cycloalkanes such as cyclopentane, cyclohexane, cycloheptane and cyclooctane; amides such as dimethylformamide and dimethylacetamide; dimethyl sulfoxide; etc. These solvents are used singly or in admixture. The solvent may contain water. The solvent is used preferably in an amount of about 0.5 to about 200 liters, more preferably about 1 to about 50 liters, per kg of the compound of the formula (1).

Although the reaction temperature varies with the material and solvent to be used and can not be determined specifically, it is usually about $-90°$ to about $100°$ C. preferably about $-78°$ C. to about $50°$ C.

The desired cephem derivative of the formula (2) can be isolated from the reaction mixture, for example, by subjecting the mixture to extraction or crystallization in the usual manner. When required, the product is further purified by a conventional method of purification such as recrystallization or column chromatography.

The present invention provides cephem derivatives of the formula (2) as desired which have introduced therein a substituent Y as selected from among various groups and which can be prepared by a simple procedure in a high yield.

The present invention will be described in greater detail with reference to the following examples. Incidentally, Ph stands for phenyl.

EXAMPLE 1

Compound of formula (5) ⟶ compound of formula (6)

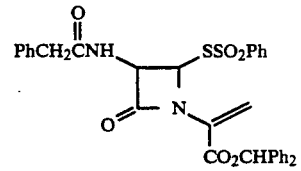

(5)

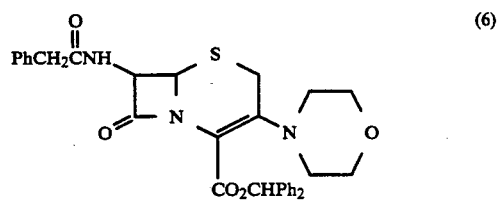

(6)

A 100 mg quantity of the compound of the formula (5) ($R^1$=phenylacetamido, $R^2$=H, $R^3$=diphenylmethyl, X=phenylsulfonyl) was dissolved in 1 ml of N,N-dimethylformamide, followed by the addition of 28 μl of morpholine to the solution and stirring at room temperature for 1 hour for reaction. The reaction mixture was subjected to extraction with ethyl acetate, and the extract was washed with water and dried over anhydrous magnesium salfate. The extract was then concentrated in a vacuum and purified by column chromatography, giving the compound of the formula (6) (R¹=phenylacetamido, R²=H, R³=diphenylmethyl, Y=morpholino) in a yield of 60%.

NMR (CDCl₃); δppm. 1.49 and 3.07 (ABq, 2H, J=14Hz), 2.81-2.91 (m, 2H), 3.07-3.17 (m, 2H), 3.56 (m, 4H), 3.70 (s, 2H), 5.01 (d, 1H, J=4Hz), 5.38 (dd, 1H, J=4Hz and 8Hz), 5 6.57 (s, 1H), 7.20-7.42 (m, 15H), 7.75 (d, 1H, J=8Hz).

EXAMPLE 2

A 100 mg quantity of the compound of the formula (5) was dissolved in 1 ml of N,N-dimethylformamide. To the solution were added 100 mg of calcium chloride and 28 μl of morpholine, and the mixture was stirred at room temperature for 1 hour for reaction. The reaction mixture was subjected to extraction with ethyl acetate, and the extract was thereafter treated in the same manner as in Example 1, giving the compound of the formula (6) in a yield of 85%. The NMR spectrum of the compound of the formula (6) obtained was perfectly in match with that of the compound obtained in Example 1.

EXAMPLE 3

Compound of formula (7) ⟶ compound of formula (8)

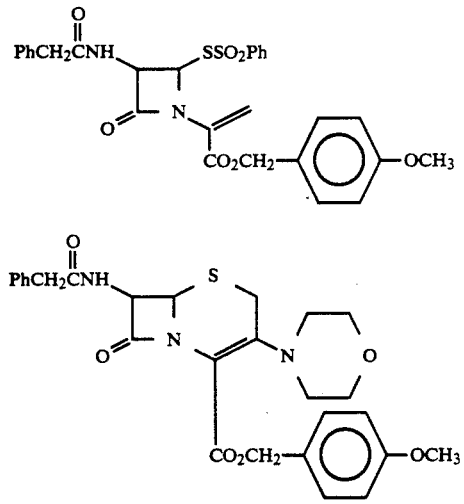

A 100 mg quantity of the compound of the formula (7) (R¹=phenylacetamido, R²=H, R³=p-methoxybenzyl, X=phenylsulfonyl) was dissolved in 1 ml of N,N-dimethylformamide. To the solution were added 100 mg of calcium chloride and 36 μl of morpholine, and the mixture was stirred at room temperature for 1 hour for reaction. The reaction mixture was subjected to extraction with ethyl acetate. The extract was thereafter treated in the same manner as in Example 1, giving the compound of the formula (8) (R¹=phenylacetamido, R²=H, R³=p-methoxybenzyl, Y=morpholino) in a yield of 87%.

NMR (CDCl₃); δppm. 2.13 and 3.00 (ABq, 2H, J=14Hz), 2.95-3.34 (m, 4H), 3.60-3.68 (m, 6H), 3.80 (s, 3H), 5.00 (d, 1H, J=4Hz), 4.87 and 5.15 (ABq, 2H, J=12Hz), 5.33 (dd, 1H, J=4Hz and 8Hz), 6.80-7.40 (m, 10H).

EXAMPLES 4 To 8

Compounds A to E were prepared by repeating the same reaction as in Example 3 with the exception of changing the nucleophilic agent from morpholine to the compounds listed in Table 1

TABLE 1

| Ex. | neucleophilic agent | Compound | yield (%) |
| --- | --- | --- | --- |
| 4 | CH₃\CHNH₂ /CH₃ | A | 78 |
| 5 | ⬡NH (pyrrolidine) | B | 80 |
| 6 | N≋N-NH (triazole) | C | 75 |
| 7 | N—N ‖ \>—SH / N—N | CH₃ | D | 72 |
| 8 | CH₃—⬠(N—N,S)—SH | E | 76 |

NMR (CDCl₃); δppm.

Compound A: 1.05 (d, 3H, J=6Hz). 1.14 (d, 3H, J=6Hz), 2.56 and 3.16 (ABq, 2H, J=15Hz), 3.12-3.20 (m, 1H), 3.63 and 3.65 (ABq, 2H, J=15Hz), 3.79 (s, 3H), 4.98 (d, 1H, J=4Hz), 4.95 and 5.17 (ABq, 2H, J=12Hz), 5.28 (dd, 1H, J=4Hz and 8Hz), 7.18 (d, 1H, J=8Hz), 6.84-7.40 (m, 9H), 8.23 (d, 1H, J=8Hz).

Compound B: 1.16-2.10 (m, 4H), 2.56 and 3.19 (ABq, 2H, J=14Hz), 3.10-3.55 (m, 4H), 3.64 (s, 2H), 3.78 (s, 3H), 5.00 (d, 1H, J=4Hz), 4.92 and 5.16 (ABq, 2H, J=12Hz), 5.37 (dd, 1H, J=4Hz and 8Hz), 6.80-7.38 (m, 9H), 7.83 (d, 1H, J=8Hz).

Compound C: 3.66 and 3.67 (ABq, 2H, J=14Hz), 3.78 (s, 2H), 3.79 (s, 3H), 5.02 and 5.04 (ABq, 2H, J=12Hz), 5.09 (d, 1H, J=5Hz), 5.93 (dd, 1H, J=5Hz and 9Hz), 6.35 (d, 1H, J=9Hz), 6.83 (d, 2H, J=6Hz), 7.13 (d, 2H, J=6Hz), 7.20-7.45 (m, 5H), 7.52 (d, 1H, J=1Hz), 7.61 (d, 1H, J=1Hz).

Compound D: 3.63 and 3.64 (ABq, 2H, J=16Hz), 3.38 and 3.80 (ABq, 2H, J=18Hz), 3.81 (s, 3H), 3.95 (s, 3H), 5.05 (d, 1H, J=5Hz), 5.22 and 5.23 (ABq, 2H, J=12Hz), 5.86 (dd, 1H, J=5Hz and 9Hz), 6.06 (d, 1H, J=9Hz), 6.85-7.40 (m, 9H).

Compound E: 2.74 (s, 3H), 3.62 and 3.64 (ABq, 2H, J=16Hz), 3.43 and 3.74 (ABq, 2H, J=18Hz), 3.80 (s, 3H), 4.98 (d, 1H, J=4Hz), 5.23 (s, 2H), 5.85 (dd, 1H, J=4Hz and 9Hz). 5.99 (d, 1H, J=9Hz), 6.82-7.40 (m, 9H).

EXAMPLE 9

Compound of formula (5) ⟶ compound of formula (9)

-continued

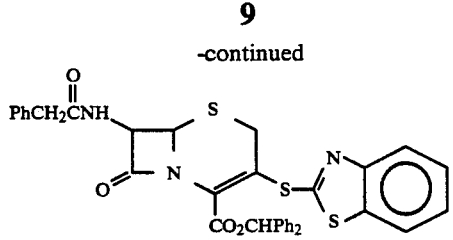
(9)

The same reaction as in Example 1 was conducted with the exception of changing the nucleophilic agent from morpholine to 2-mercaptobenzothiazole to obtain the compound the formula (9) ($R^1$=phenylacetamido, $R^2$=H, $R^3$=diphenylmethyl, Y=benzothiazol-2-ylthio) in a yield of 74%.

NMR (CDCl$_3$); δppm. 3.62 and 3.65 (ABq, 2H, J=16Hz), 3.50 and 3.85 (ABq, 2H, J=18Hz), 5.05 (d, 1H, J=5Hz), 5.91 (dd, 1H, J=5Hz and 9Hz), 6.22 (d, 1H, J=9Hz), 6.98 (s, 1H), 7.20–8.00 (m, 19H).

EXAMPLE 10

Compound of formula (10) ⟶ compound of formula (9)

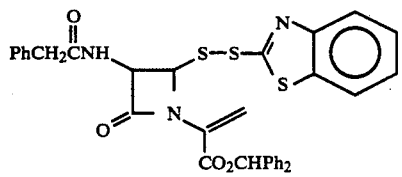
(10)

The compound of the formula 10($R^1$=phenylacetamido, $R^2$=H, $R^3$=diphenylmethyl, X=benzothiazol-2-ylthio) in an amount of 100 mg was dissolved in 1 ml of N,N-dimethylformamide. To the solution were added 100 mg of calcium chloride and 2 mg of 2-mercaptobenzothiazole, and the mixture was stirred at room temperature for 1 hour. The reaction mixture was treated in the same manner as in Example 1 to obtain the compound of the formula (9) in a yield of 70%. The NMR spectrum of the compound of the formula (9) was in match with that of the compound obtained in Example 9.

EXAMPLE 11

Compound of formula (7) ⟶ compound of formula (11)

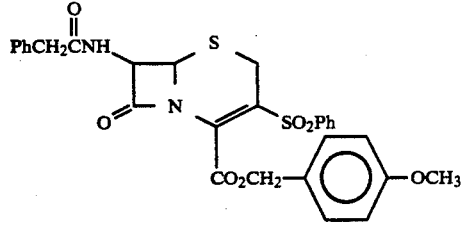
(11)

A 100 mg quantity of the compound of the formula (7) was dissolved in 1 ml of N,N-dimethylformamide. To the solution were added 100 mg of calcium oxide and 5 mg of benzenesulfinic acid, and the mixture was stirred at room temperature for 1 hour for reaction. The reaction mixture was thereafter treated in the same manner as in Example 1, giving the compound of the formula (11) ($R^1$=phenylacetamido, $R^2$=H, $R^3$=p-methoxybenzyl, Y=phenylsulfonyl) in a yield of 87%.

NMR (CDCl$_3$); δppm. 3.33 and 3.49 (ABq, 2H, J=18Hz), 3.58 and 3.60 (ABq, 2H, J=16Hz), 3.81 (s, 3H), 4.91 (d, 1H, J=5Hz), 5.36 (s, 2H), 5.85 (dd, 1H, J=5Hz and 9Hz), 6.06 (d, 1H, J=9Hz), 6.87–7.96 (m, 14H).

EXAMPLE 12

Compound of formula (5) ⟶ compound of formula (12)

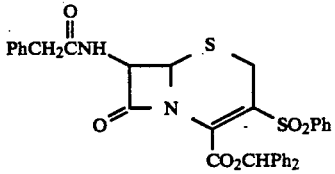
(12)

The same reaction as in Example 11 was conducted with the exception of using the compound of the formula (5) in the compound of the formula (7), giving the compound of the formula (12) ($R^1$=phenylacetamido, $R^2$=H, $R^3$=diphenylmethyl, Y=phenylsulfonyl) in a yield of 70%.

NMR (CDCl$_3$); δppm. 3.53 and 3.56 (ABq, 2H, J=18Hz), 3.58 and 3.61 (ABq, 2H, J=15Hz), 4.95 (d, 1H, J=5Hz), 5.85 (dd, 1H, J=5Hz and 9Hz), 5.93 (d, 1H, J=9Hz), 7.08 (s, 1H), 7.20–7.88 (m, 20H).

EXAMPLE 13

Compound of formula (5) ⟶ compound of formula (13)

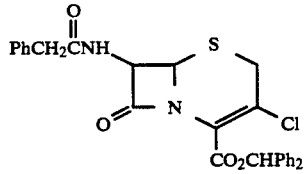
(13)

A 100 mg quantity of the compound of the formula (5) was dissolved in 1 ml of N,N-dimethylformamide. To the solution were added 100 mg of calcium chloride and 10 mg of lithium chloride, and the mixture was stirred at room temperature for 2 hours for reaction. The reaction mixture was thereafter treated in the same manner as in Example 1, giving the compound of the formula (13) ($R^1$=phenylacetamido, $R^2$=H, $R^3$=diphenylmethyl, Y=Cl) in a yield of 71%.

NMR (CDCl$_3$); δppm. 3.63 and 3.65 (ABq, 2H, J=16Hz), 3.44 and 3.75 (ABq, 2H, J=18Hz), 5.01 (d, 1H, J=5Hz), 5.83 (dd, 1H, J=5Hz and 9Hz), 6.09 (d, 1H, J=9Hz), 6.98 (s, 1H), 7.21–7.40 (m, 15H).

EXAMPLE 14

Compound of formula (7) ⟶ compound of formula (14)

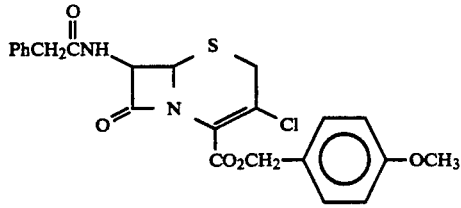
(14)

The same reaction as in Example 13 was conducted with the exception of using the compound of the formula (7) in place of the compound of the formula (5), giving the compound of the formula (14) ($R^1$=phenylacetamido, $R^2$H, $R^3$=p-methoxybenzyl, Y=Cl) in a yield of 70%.

NMR (CDCl$_3$); ppm. 3.63 and 3.65 (ABq, 2H, J=16Hz), 3.42 and 3.74 (ABq, 2H, J=19Hz), 3.80 (s, 3H), 4.98 (d, 1H, J=5Hz), 5.22 (s, 2H), 5.80 (dd, 1H, J=5Hz and 9Hz), 6.03 (d, 1H, J=9Hz), 6.85–7.40 (m, 9H).

We claim:

1. A process for preparing a cephem compound of the formula

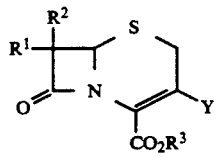

wherein $R^1$ is amino or protected amino; $R^2$ is hydrogen or lower alkoxyl; $R^3$ is hydrogen or a carboxylic acid protecting group; and Y is halogen, hydroxyl, azido, cyano or isocyano; or —OR$^7$, —OCOR$^7$, —SCSOR$^7$, —SCSN(R$^7$)$_2$, —NHR$^7$, —N(R$^7$)$_2$ or —SO$_2$R$^7$, wherein $R^7$ is lower alkyl, phenyl or naphthyl; or —SR$^8$, wherein $R^8$ is lower alkyl, phenyl, naphthyl, piperidino, morpholino, 1-piperazinyl, 1-pyrrolidinyl, 1-imidazolidinyl, 1-pyrazolidinyl, 2-pyrrolin-1-yl, 2-imidazolin-1-yl, 3-pyrazolin-1-yl, 1-indolinyl, 2-indolinyl, 1-pyrrolyl, 1-indolyl, 2-isoindolyl, 1-imidazolyl, 1-pyrazolyl, 1-benzimidazolyl, 1H-1-indazolyl, 1-triazolyl or 1-tetrazolyl; optionally substituted by halogen, hydroxyl, nitro, cyano, aryl, lower alkyl, amino, mono lower alkylamio, di lower alkylamino, mercapto, lower alkyl alkylthio, arylthio, formyl or formyloxy; R$^6$COO—, R$^6$CO—, R$^6$O— or R$^6$OCO—, wherein R$^6$ is lower alkyl phenyl or naphthyl, which comprises reacting an allenyl β-lactam of the formula

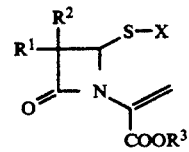

wherein $R^1$, $R^2$ and $R^3$ are as defined above; and X is —SO$_2$R$^4$ or —SR$^4$, wherein R$^4$ represents phenyl, naphthyl, thiazol-2-yl, thiadiazol-2-yl, benzothiazol-2-yl, oxazol-2-yl, benzoxazol-2-yl, imidazol-2-yl, benzoimidazol-2-yl, pyrimidinyl or pyridyl, optionally substituted by halogen, hydroxyl, nitro, cyano, aryl, lower alkyl, amino, mono lower alkylamio, di lower alkylamino, mercapto, lower alkyl alkylthio, arylthio, formyl or formyloxy; or R$^6$COO—, R$^6$CO—, R$^6$O— or R$^6$OCO—, wherein R$^6$ is lower alkyl, phenyl or naphthyl; with H—Y.

* * * * *